United States Patent
Riediger

(10) Patent No.: US 10,311,212 B2
(45) Date of Patent: Jun. 4, 2019

(54) NUTRIENT VALUE LOSS TRACKING SYSTEM AND METHOD

(71) Applicant: Eileen Riediger, Heidelberg (DE)

(72) Inventor: Eileen Riediger, Heidelberg (DE)

(73) Assignee: SAP SE, Walldorf (DE)

( * ) Notice: Subject to any disclaimer, the term of this patent is extended or adjusted under 35 U.S.C. 154(b) by 1596 days.

(21) Appl. No.: 14/086,422

(22) Filed: Nov. 21, 2013

(65) Prior Publication Data

US 2015/0044643 A1 Feb. 12, 2015

Related U.S. Application Data

(60) Provisional application No. 61/864,773, filed on Aug. 12, 2013.

(51) Int. Cl.
*G06F 19/00* (2018.01)

(52) U.S. Cl.
CPC .................. *G06F 19/3475* (2013.01)

(58) Field of Classification Search
None
See application file for complete search history.

(56) References Cited

U.S. PATENT DOCUMENTS

| | | | |
|---|---|---|---|
| 5,233,520 A | 8/1993 | Kretsch et al. | |
| 5,558,742 A * | 9/1996 | Kiefer | G01N 33/02 156/244.16 |
| 6,038,546 A * | 3/2000 | Ferro | G06Q 30/06 705/15 |
| 6,451,360 B2 | 9/2002 | Bailey et al. | |
| 7,579,037 B2 | 8/2009 | Pons Biescas et al. | |
| 7,757,203 B2 | 7/2010 | Scholl et al. | |
| 2002/0124017 A1 | 9/2002 | Mault | |
| 2003/0195779 A1 | 10/2003 | Scholl et al. | |
| 2004/0161522 A1 | 8/2004 | Toves | |
| 2005/0137725 A1 | 6/2005 | Scholl et al. | |
| 2005/0137928 A1 | 6/2005 | Scholl et al. | |
| 2006/0251791 A1 | 11/2006 | Rubio et al. | |
| 2009/0246323 A1 | 10/2009 | Pons Biescas et al. | |

(Continued)

OTHER PUBLICATIONS

Prabhu et al., "Effects of storage condition and domestic cooking on the quality and nutrient content of African leafy vegetables (*Cassia tora* and *Corchorus tridens*)", Journal of the Science of Food and Agriculture, vol. 89, Issue 10, Aug. 2009, pp. 1709-1721.*

(Continued)

*Primary Examiner* — Aniss Chad
*Assistant Examiner* — Bernard E Cothran
(74) *Attorney, Agent, or Firm* — Schwegman Lundberg & Woessner, P.A.

(57) ABSTRACT

A system and method include exploding a recipe via a computer system for a process to make an end food product into a set of hierarchical process steps, obtaining nutrient values for each input material to be used in making the end food product, obtaining loss profiles for input materials, the nutrient loss profiles including a process loss profile for steps in the process to make the end food product and a storage loss profile for storing intermediate food product resulting during the process, and performing a hierarchical based nutrient loss calculation using the nutrient values and loss profiles to quantify nutrients remaining in the end food product.

20 Claims, 7 Drawing Sheets

(56) References Cited

U.S. PATENT DOCUMENTS

| | | |
|---|---|---|
| 2010/0062402 A1 | 3/2010 | Miller-Kovach et al. |
| 2010/0082132 A1* | 4/2010 | Marruchella .... G05B 19/41835 |
| | | 700/86 |
| 2011/0202359 A1 | 2/2011 | Rak |
| 2012/0215333 A1 | 8/2012 | Scholl et al. |

OTHER PUBLICATIONS

Shai et al., "Adaptation of international nutrition databases and data-entry system tools to a specific population", Public Health Nutrition, vol. 6, Issue 4, Jun. 2003, pp. 401-406.*

* cited by examiner

300 ─╮

| RECIPE | STAGE | ITEM TYPE | SPEC. | QUANTITY | UOM | PROCESS LOSS PROFILE | STORAGE LOSS PROFILE |
|---|---|---|---|---|---|---|---|
| 1 | | PO | PO1 | 100 | G | PL10 | SL5 |
| 1 | | IN | M1 | 10 | G | | |
| 1 | | IN | M2 | 90 | G | | |
| | | | | | | | |
| 2 | 1 | PO | M2 | 100 | G | PL5 | SL10 |
| 2 | 1 | IN | M3 | 50 | G | | |
| 2 | 1 | IN | M4 | 20 | G | | |
| 2 | 1 | IS | S1 | 30 | G | | |
| 2 | 2 | OS | S1 | 100 | G | PL10 | |
| 2 | 2 | IN | M5 | 50 | G | | |
| 2 | 2 | IN | M6 | 50 | G | | |
| | | | | | | | |
| 1 | | PO | M5 | 100 | G | PL5 | SL5 |
| 1 | | IN | M7 | 80 | G | | |
| 1 | | IN | M8 | 20 | G | | |

| SPEC. | NUTRIENT | QUANTITY PER 100 G |
|---|---|---|
| M1 | VIT_C | 5 MG |
| M1 | VIT_A | 10 MG |
| M3 | VIT_C | 10 MG |
| M4 | VIT_C | 15 MG |
| M4 | VIT_A | 5 MG |
| M8 | VIT_C | 3 MG |
| M8 | VIT_A | 2 MG |

| PROFILE | NUTRIENT | LOSS |
|---|---|---|
| PL10 | VIT_C | 10% |
| PL5 | VIT_C | 5% |
| SL10 | VIT_C | 10% |
| SL5 | VIT_C | 5% |

*FIG. 5*

| RFO_GUID | ST_ID | SUBID | FLG_PO | STREAM_PO | UOM | QUANT_AGGR |
|---|---|---|---|---|---|---|
| 1 | 0 | PO1 | X | | G | -100 |
| 1 | 0 | M1 | | | G | 10 |
| 1 | 0 | M2 | | | G | 90 |
| 2 | 1 | M2 | X | | G | -90 |
| 2 | 1 | M3 | | | G | 45 |
| 2 | 1 | M4 | | | G | 18 |
| 2 | 1 | S1 | | | G | 27 |
| 2 | 2 | S1 | | X | G | -27 |
| 2 | 2 | M5 | | | G | 13,5 |
| 2 | 2 | M6 | | | G | 13,5 |
| 3 | 0 | M5 | X | | G | -13,5 |
| 3 | 0 | M7 | | | G | 10,8 |
| 3 | 0 | M8 | | | G | 2,7 |

FIG. 9

| RFO_GUID | ST_ID | SUBID | FLG_OUT | UOM | QUANT_AGGR | CALCULATION NUTRIENT VALUE | VITAMIN C [MG] |
|---|---|---|---|---|---|---|---|
| 3 | 0 | M8 |   | G | 2,7 | (2,7G/100G*3MG)*0,95 | 0,07695 |
| 3 | 0 | M7 |   | G | 10,8 | 0 * 0,95 | 0 |
| 3 | 0 | M5 | X | G | -13,5 | SUM | 0,07695 |
| 2 | 2 | M6 |   | G | 13,5 | 0 * 0,9 | 0 |
| 2 | 2 | M5 |   | G | 13,5 | CARRYOVER*0,9 | 0,069255 |
| 2 | 2 | S1 | X | G | -27 | SUM | 0,069255 |
| 2 | 1 | S1 |   | G | 27 | CARRYOVER*0,9 | 0,06579225 |
| 2 | 1 | M4 |   | G | 18 | (18G/100G*15MG)*0,95 | 2,565 |
| 2 | 1 | M3 |   | G | 45 | (45G/100G*10MG)*0,95 | 4,275 |
| 2 | 1 | M2 | X | G | -90 | SUM | 6,90579225 |
| 1 | 0 | M2 |   | G | 90 | CARRYOVER*0,9 | 6,21521 |
| 1 | 0 | M1 |   | G | 10 | (10G/100G*5MG)*0,9 | 0,45 |
| 1 | 0 | P01 |   | G | -100 | SUM | 6,66521 |

*FIG. 10*

| RFO | ST_ID | SUBID | FLG_OUT | UOM | QUANT_AGGR | VITAMIN C [MG] | CALCULATION STORAGE LOSS | VITAMIN C AFTER STORAGE LOSS [MG] |
|---|---|---|---|---|---|---|---|---|
| 3 | 0 | M8 | | G | 2,7 | 0,07695 | 0,07695*0,95 | 0,073102 |
| 3 | 0 | M7 | | G | 10,8 | | | |
| 3 | 0 | M5 | X | G | -13,5 | 0,07695 | SUM | 0,073102 |
| 2 | 2 | M6 | | G | 13,5 | | | |
| 2 | 2 | M5 | | G | 13,5 | 0,069255 | 0,069255 | 0,069255 |
| 2 | 2 | S1 | X | G | -27 | 0,069255 | SUM | 0,069255 |
| 2 | 1 | S1 | | G | 27 | 0,065792 | 0,065792*0,9 | 0,59213 |
| 2 | 1 | M4 | | G | 18 | 2,565 | 2,565*0,9 | 2,3085 |
| 2 | 1 | M3 | | G | 45 | 4,275 | 4,275*0,9 | 3,8475 |
| 2 | 1 | M2 | X | G | -90 | 6,905792 | SUM | 6,215213 |
| 1 | 0 | M2 | | G | 90 | 6,21521 | 6,21521*0,95 | 5,904449 |
| 1 | 0 | M1 | | G | 10 | 0,45 | 0,45*0,95 | 0,4275 |
| 1 | 0 | PO1 | | G | -100 | 6,66521 | SUM | 6,331949 |

*FIG. 11*

NUTRIENT VALUE LOSS TRACKING SYSTEM AND METHOD

RELATED APPLICATION

This application claims priority to U.S. Provisional Application Ser. No. 61/864,773 (entitled Nutrient Value Loss Tracking System and Method, filed Aug. 12, 2013) which is incorporated herein by reference.

BACKGROUND

During a manufacturing process of a product, nutrients are destroyed due to process steps like heating. This destruction of nutrients is called process loss, as less nutrient value is available in the end product than the sum of the nutrient values of the product's input specifications. Nutrients can also be destroyed due to storage of a product. This destruction is called storage loss. Prior loss calculations are only taken into account after nutrient values have been calculated for the end product. However, these calculations may not take into account losses that occur during storage of semi-finished products.

SUMMARY

A method includes exploding a recipe via a computer system for a process to make an end food product into a set of hierarchical process steps, obtaining nutrient values for each input material to be used in making the end food product, obtaining loss profiles for input materials, the nutrient loss profiles including a process loss profile for steps in the process to make the end food product and a storage loss profile for storing intermediate food product resulting during the process, and performing a hierarchical based nutrient loss calculation using the nutrient values and loss profiles to quantify nutrients remaining in the end food product.

A computer readable storage device has instructions for causing a computer to perform a method. The method includes exploding a recipe via a computer system for a process to make an end food product into a set of hierarchical process steps, obtaining nutrient values for each input material to be used in making the end food product, obtaining loss profiles for input materials, the nutrient loss profiles including a process loss profile for steps in the process to make the end food product and a storage loss profile for storing intermediate food product resulting during the process, and performing a hierarchical based nutrient loss calculation using the nutrient values and loss profiles to quantify nutrients remaining in the end food product.

A system includes a processor and a storage device coupled to the processor. The storage device has a program to perform a method when executed by the processor. The method includes exploding a recipe via a computer system for a process to make an end food product into a set of hierarchical process steps, obtaining nutrient values for each input material to be used in making the end food product, obtaining loss profiles for input materials, the nutrient loss profiles including a process loss profile for steps in the process to make the end food product and a storage loss profile for storing intermediate food product resulting during the process, and performing a hierarchical based nutrient loss calculation using the nutrient values and loss profiles to quantify nutrients remaining in the end food product.

BRIEF DESCRIPTION OF THE DRAWINGS

FIG. 3 is a table illustrating recipes illustrating ingredients, process loss profiles, and storage loss profiles according to an example embodiment.

FIG. 4 is a table illustrating materials used along with nutrient values according to an example embodiment.

FIG. 5 is a table illustrating nutrient loss profiles according to an example embodiment.

FIG. 9 is a system internal representation of a result of an explosion of a recipe according to an example embodiment.

FIG. 10 is a table illustrating a sample nutrient calculation for vitamin C according to an example embodiment.

FIG. 11 is a table illustrating a storage loss calculation for vitamin C according to an example embodiment.

DETAILED DESCRIPTION

In the following description, reference is made to the accompanying drawings that form a part hereof, and in which is shown by way of illustration specific embodiments which may be practiced. These embodiments are described in sufficient detail to enable those skilled in the art to practice the invention, and it is to be understood that other embodiments may be utilized and that structural, logical and electrical changes may be made without departing from the scope of the present invention. The following description of example embodiments is, therefore, not to be taken in a limited sense, and the scope of the present invention is defined by the appended claims.

The functions or algorithms described herein may be implemented in software or a combination of software and human implemented procedures in one embodiment. The software may consist of computer executable instructions stored on computer readable media such as memory or other type of storage devices. Further, such functions correspond to modules, which are software, hardware, firmware or any combination thereof. Multiple functions may be performed in one or more modules as desired, and the embodiments described are merely examples. The software may be executed on a digital signal processor, ASIC, microprocessor, or other type of processor operating on a computer system, such as a personal computer, server or other computer system.

During a manufacturing process of a food product, nutrients are destroyed due to process steps like heating. This destruction of nutrients is called process loss as less nutrient value is available in the end product than the sum of the nutrient values of the product's input specifications. Nutrients can also be destroyed due to storage of a product. This destruction is called storage loss.

Prior nutrient losses are only taken into account after the nutrient values are already calculated for the end product.

But process and storage loss happen in between at different process steps or stages of manufacture and also at semi-finished product levels. The process/storage loss calculation is a hierarchical loss calculation utilizing a specification description containing information about the nutrient values of each input material used in making the product. Each process step used to make the product has an associated loss profile that contains information regarding how much nutrient value is lost in the step. With the loss profile information and the specification information of each input material, a loss calculation may be done.

Figure 1:
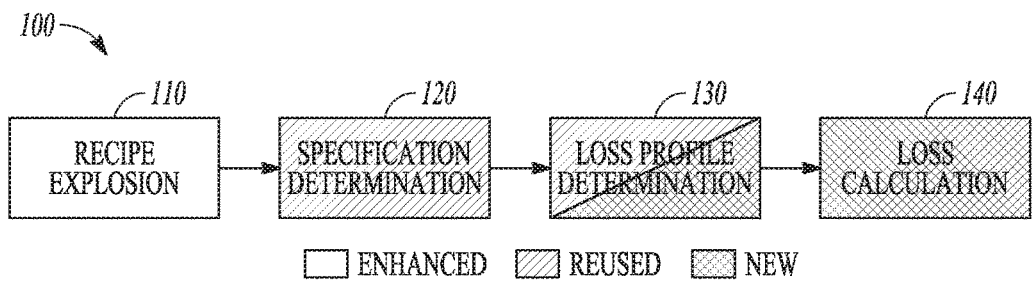
FIG. 1 is a block flow diagram of components that perform a nutrient loss calculation according to an example embodiment.

In one embodiment, a computer executable application 100 is illustrated in block form in FIG. 1, and performs a loss calculation that contains four functional blocks. A recipe explosion block 110 explodes a recipe down to raw specifications like sugar. That means that if an input specification is a semi-finished product then the explosion searches for the corresponding recipe of the product and drills into their input materials.

A specification determination block is shown at 120. For each raw specification the nutrient values are determined by specification block 120. An existing application may be used to obtain correct nutrient values.

A loss profile determination block is shown at 130. For each recipe output or stage output the assigned loss profile is determined by loss profile determination block 130. An environmental health and safety application may be used to get the profile values, e.g. that 10% vitamin C gets lost during a process step. Other sources of information may also be utilized to determine profile values, such as studies conducted by universities and other research institutions in further embodiments.

A hierarchical loss calculation block is shown at 140. Out of the explosion result, the nutrient values of each specification and the loss profile information the nutrient value for the primary output is calculated in a hierarchical manner using block 140. Some parts of an existing application program nutrient calculation method may be reused or enhanced for the new hierarchical loss calculation block 140.

Figure 2:
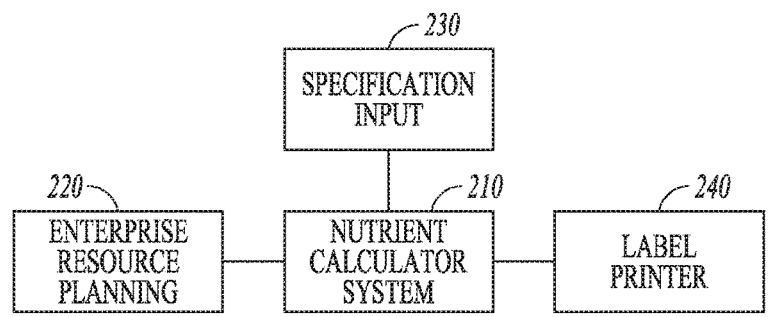
FIG. 2 is a block diagram of a system to perform a nutrient loss calculation according to an example embodiment.

FIG. 2 illustrates a system that includes a nutrient calculator system 210, enterprise resource planning system 220, specification input 230, and label printer 240. The nutrient calculator system 210 receives a recipe from the enterprise resource planning system 220 and uses it, along with a specification input 230 to perform the hierarchical nutrient loss calculation. The specification input 230 may include a data entry device to enter specifications for various ingredients used in the recipe as obtained from different sources, such as vendors. The input 230 may be from a vendor system coupled by network in some embodiments. The label printer 240 receives a label with final calculated nutrient content for printing food labels required by various regulations.

The following example illustrated in table 300 in FIG. 3 is helpful to explain the loss calculation. Table 300 includes several columns indicating a recipe number 310, stage number 315, item type 320, specification identifier 325, quantity 330, UOM (unit of measure) 335, process loss profile identifier 340, and storage loss identifier 345. Table 300 includes various item types 320 such as PO—primary output, IN—input item, IS—input stream, and OS—output stream. Table 300 columns provide information utilized for the loss calculation.

Separate tables are provided for the specification of materials at 400 in FIG. 4 showing a specification identifier 410, nutrient 415 and quantity 420, and a loss profiles table at 500 in FIG. 5 showing a profile identifier 510, nutrient 515 and associated loss 520.

There are three recipes. Two of them do not contain a process step. One contains two process steps with an output stream on a second stage which is consumed in the first stage. There is no fork and join or rework in this example, however, forks and joins may be accommodated in further embodiments. The maintenance of process and storage loss profiles on stage level may be done via databases, and accessed via processes executing on a computer system in some embodiments.

Figure 6:
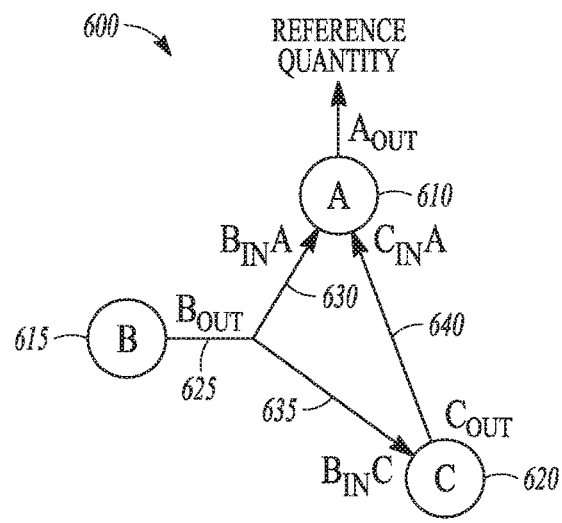
FIG. 6 is a graph illustrating input and output flows according to an example embodiment.

The recipe explosion in one embodiment may be based on a graph and matrix calculation. The graph illustrated at 600 in FIG. 6 shows an algorithm having input and output flows between recipes indicated at (A) 610, (B) 615, and (C) 620. Recipe B at 615 outputs $B_{OUT}$ at 625, which is split into two inputs. A first input, $B_{IN}A$ at 630 is received by recipe A at 610. The remainder of $B_{OUT}$ is provided as $B_{IN}C$ to recipe C at 620, which produces $C_{OUT}$ at 640 which is provided as $C_{IN}A$ to recipe A at 610.

Figure 7:
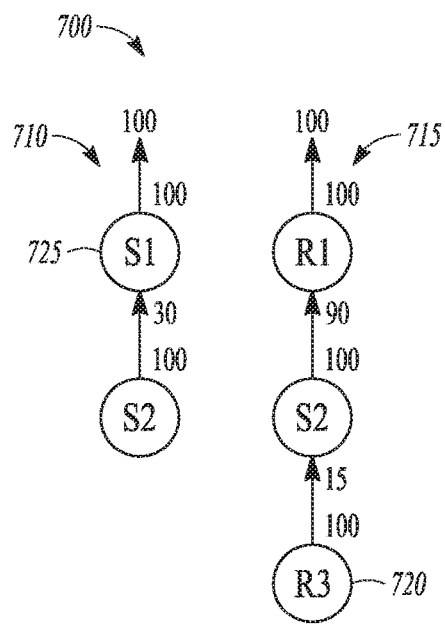
FIG. 7 is a graphical representation of an explosion of a recipe according to an example embodiment.

If the recipe explosion determines a recipe that contains streams then this recipe is exploded itself as shown in FIG. 7 at 700. According to this algorithm the example described above contains two graphs, a first graph 710 and a second graph 715. The first graph 710 for the explosion of recipe 2 is used to bring all quantities of recipe 2 to the quantity of the primary output M2. The result of that explosion is than represented in the second graph 715 for the whole explosion as the primary output of recipe 3 at 720 only brings 15 G into recipe 2 instead of 30 G.

Figure 8:
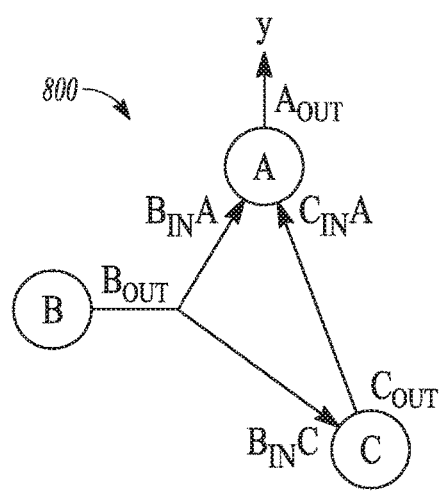
FIG. 8 is a graphical representation of an explosion of a recipe according to an example embodiment.

FIG. 8 is a graph illustrating an explosion of a recipe at 800 resulting in an output, y. In order to get the aggregated component list for each component, factors for the outputs have to be calculated. A factor of an output reflects the sum of the weighted quantities where this output serves as an input. According to this rule an equation system with n equations and n factors is built up. The effort of this calculation is the calculation on real quantities, because with the calculated factor also components with unit of measurement "piece" can be multiplied. The only restriction for building the equation system is the same unit of measurement.

The algorithm is the following $B_{out}A = \Sigma B_{in}X \times f_X$ $B_{out}A$ corresponds to the primary output of recipe B. Since B is used by both A and C, the summation corresponds to both of such recipes times a factor $f_X$ to account for measurement conversions. According to that the equation system is the following:

$$B_{out} \times F_B = B_{in}A \times f_A + B_{in}C \times F_C \qquad \text{I)}$$

$$C_{out} \times F_C = C_{in}A \times f_A \qquad \text{II)}$$

$$A_{out} \times F_A = y \qquad \text{III)}$$

With the equations a matrix can be built:

$$\begin{pmatrix} -B_{out} & B_{in}A & B_{in}C \\ 0 & C_{in}A & -C_{out} \\ 0 & 0 & A_{out} \end{pmatrix} \times \begin{pmatrix} f_B \\ f_C \\ f_A \end{pmatrix} = \begin{pmatrix} 0 \\ 0 \\ y \end{pmatrix}$$

The Matrix may be transformed into reduced row echelon form. Afterwards the factors can be calculated through back substitution. In the end the formulas have to be calculated with their factor.

For the example this means:

$$100 \times f_{R3} = 15 \times f_{R2} \qquad \text{I)}$$

$$100 \times f_{R2} = 90 \times f_{R1} \qquad \text{II)}$$

$$100 \times f_{R1} = 100 \qquad \text{III)}$$

$$\begin{pmatrix} -100 & 15 & 0 \\ 0 & -100 & 90 \\ 0 & 0 & 100 \end{pmatrix} \times \begin{pmatrix} f_{R3} \\ f_{R2} \\ f_{R1} \end{pmatrix} = \begin{pmatrix} 0 \\ 0 \\ 100 \end{pmatrix}$$

$$f_{R1} = 1$$
$$f_{R2} = 0.9$$
$$f_{R3} = 0,135$$

Therefore the result of the explosion in a system internal representation of similar information from Table 300 is shown in a Table 900 in FIG. 9.

RFO_GUID 910 is the recipe id, ST_ID 915 is the stage id, SUBID 920 is the specification ID, FLG_PO 925 is a flag for the primary output, STREAM_PO 930 is a flag for the stream output, UOM 935 is unit of measure and QUANT_AGGR 940 is a quantity aggregation amount. In the current explosion the lines for the input and output stream S1 at 725 would not be there but the lines are very important for the new calculation. Therefore a new type of explosion with a new class implementation behind has to be created which brings out all intermediate streams.

The specification determination is reused as only the nutrient values per specification is retrieved in one embodiment, which is similar to prior calculations around nutrients.

For the loss profile determination, the profile settings determination can be reused. As a profile is a specification the specification determination may be used. A new loss profile assignment determination may be used. With the result of the explosion, each involved primary output and stream output can be identified. Afterwards a recipe application programming interface can be asked for the assigned loss profile.

With all the information about the explosion, the nutrient values per specification, the assigned loss profiles and the loss profile settings, the calculation can be done item by item with summation on each stage and recipe output.

In mathematical theory this means:

$$\text{NutrientValueInclProcessLoss}_{Primary\ Output} = \Sigma(\text{NutrientValue}_{InputItem} \times \text{ProcessLoss})$$

In case the input item is not produced in an underlying recipe then the term NutrientValue$_{InputItem}$ is the following:

$$\text{NutrientValue}_{InputItem} = \frac{\text{Quantity}_{InputItem}}{\text{ReferenceQuantity}_{Nutrient}} \times \text{NutrientValue}_{InputItem}$$

In case the input item is a product of an underlying recipe then the term NutrientValue$_{InputItem}$ is the following:

$$\text{NutrientValue}_{InputItem} = \text{NutrientValue}_{PrimaryOutputOfUnderlyingRecipe}$$

Considering the example a Table 1000 in FIG. 10 shows an example calculation for Vitamin C. Table 1000 includes several columns having labels that are the same as table 900 and are numbered accordingly. Additional columns include a FLG_OUT column 1010, calculation nutrient value column 1015 and Vitamin C [MG] column 1020. The storage loss is calculated on top of the process loss. That means the storage loss is calculated as: NutrientVaqlueInclStorageLoss=NutrientValueInclProcessLoss×StorageLoss. A table 1100 in FIG. 11 illustrates example calculations for Vitamin C, and includes several columns with reference numbers consistent with tables 900 and 1000. In addition, a calculation storage loss column 1110 and a vitamin C after storage loss in MG column 1115 are provided.

Note that the storage loss can be calculated for storage of materials prior to use in the recipe, between stages of a recipe, and following completion of the recipe based on an estimated shipping time prior to being made available in a retail store.

Figure 12:
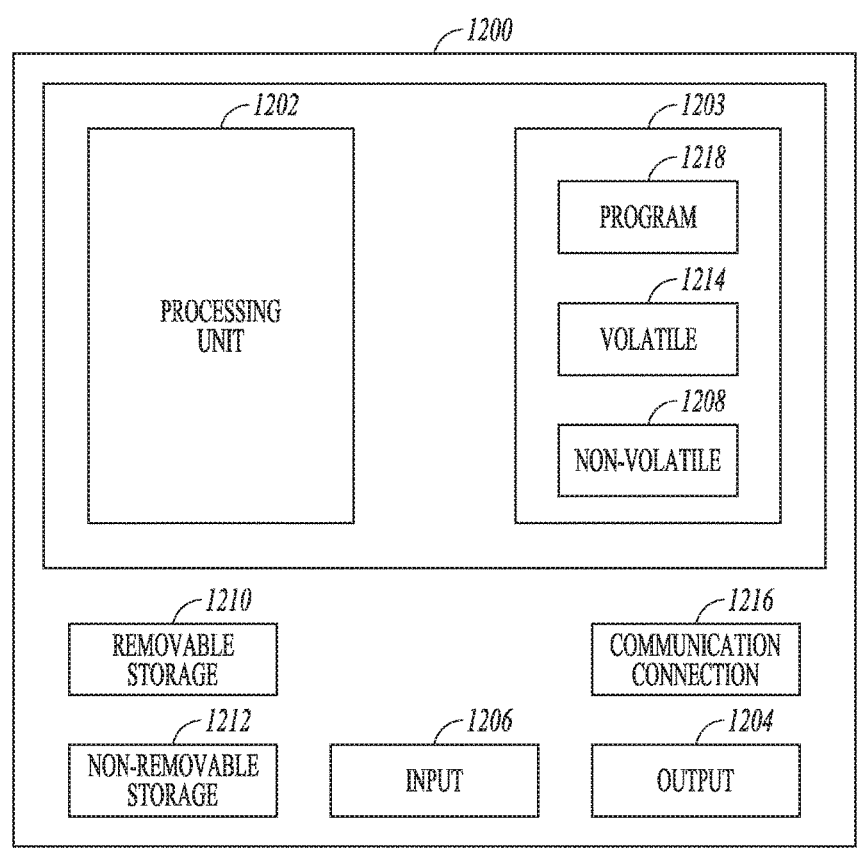
FIG. 12 is a block diagram of a computer system for performing methods and calculating losses according to an example embodiment.

FIG. 12 is a block schematic diagram of a computer system 1200 to implement one or more algorithms according to an example embodiment. In one embodiment, multiple such computer systems are utilized in a distributed network to implement multiple components in a transaction based environment. An object-oriented, service-oriented, or other architecture may be used to implement such functions and communicate between the multiple systems and components.

One example computing device in the form of a computer 1200, may include a processing unit 1202, memory 1203, removable storage 1210, and non-removable storage 1212. Memory 1203 may include volatile memory 1214 and non-volatile memory 1208. Computer 1200 may include—or have access to a computing environment that includes—a variety of computer-readable media, such as volatile memory 1214 and non-volatile memory 1208, removable storage 1210 and non-removable storage 1212. Computer storage includes random access memory (RAM), read only memory (ROM), erasable programmable read-only memory (EPROM) & electrically erasable programmable read-only memory (EEPROM), flash memory or other memory technologies, compact disc read-only memory (CD ROM), Digital Versatile Disks (DVD) or other optical disk storage, magnetic cassettes, magnetic tape, magnetic disk storage or other magnetic storage devices, or any other medium capable of storing computer-readable instructions. Computer 1200 may include or have access to a computing environment that includes input 1206, output 1204, and a communication connection 1216. The computer may operate in a networked environment using a communication connection to connect to one or more remote computers, such as database servers. The remote computer may include a personal computer (PC), server, router, network PC, a peer device or other common network node, or the like. The communication connection may include a Local Area Network (LAN), a Wide Area Network (WAN) or other networks.

Computer-readable instructions stored on a computer-readable medium are executable by the processing unit 1202 of the computer 1200. A hard drive, CD-ROM, and RAM are some examples of articles including a non-transitory computer-readable medium. For example, a computer program 1218 capable of providing a generic technique to perform access control check for data access and/or for doing an operation on one of the servers in a component object model (COM) based system may be included on a CD-ROM and loaded from the CD-ROM to a hard drive. The computer-readable instructions allow computer 1200 to provide generic access controls in a COM based computer network system having multiple users and servers.

EXAMPLES

1. A method comprising:
exploding a recipe, via a computer system for a process to make an end food product, into a set of hierarchical process steps;
obtaining nutrient values for each input material to be used in making the end food product;
obtaining nutrient loss profiles for input materials, the nutrient loss profiles including a process loss profile for steps in the process to make the end food product and a storage loss profile for storing intermediate food product resulting during the process; and
performing a hierarchical based nutrient loss calculation using the nutrient values and loss profiles to quantify nutrients remaining in the end food product.

2. The method of example 1 wherein storage losses are calculated on top of process losses.

3. The method of any of examples 1-2 wherein the process loss profile is a percentage of a nutrient value lost during a process step.

4. The method of any of examples 1-3 wherein a storage loss profile is a percentage of nutrient value lost during storage of a material.

5. The method of any of examples 1-4 wherein performing a hierarchical nutrient loss calculation comprises building an equation system for each process output.

6. The method of example 5 wherein exploding the recipe results in a graph showing the input and output flows between stages of the recipe.

7. The method of example 6 wherein the equation systems are built into a matrix based on the graph.

8. The method of example 7 wherein the matrix is transformed into reduced row echelon form.

9. A computer readable storage device having instructions for causing a computer to execute a method, the method comprising:
exploding a recipe for a process to make an end food product, into a set of hierarchical process steps;
obtaining nutrient values for each input material to be used in making the end food product;
obtaining nutrient loss profiles for input materials, the nutrient loss profiles including a process loss profile for steps in the process to make the end food product and a storage loss profile for storing intermediate food product resulting during the process; and
performing a hierarchical based nutrient loss calculation using the nutrient values and loss profiles to quantify nutrients remaining in the end food product.

10. The computer readable storage device of example 9 wherein storage losses are calculated on top of process losses.

11. The computer readable storage device of any of examples 9-10 wherein the process loss profile is a percentage of a nutrient value lost during a process step.

12. The computer readable storage device of any of examples 9-11 wherein a storage loss profile is a percentage of nutrient value lost during storage of a material.

13. The computer readable storage device of any of examples 9-12 wherein performing a hierarchical nutrient loss calculation comprises building an equation system for each process output.

14. The computer readable storage device of example 13 wherein exploding the recipe results in a graph showing the input and output flows between stages of the recipe.

15. The computer readable storage device of example 14 wherein the equation systems are built into a matrix based on the graph.

16. The computer readable storage device of example 15 wherein the matrix is transformed into reduced row echelon form.

17. A system comprising:
a processor;
a storage device coupled to the processor, the storage device having a program to perform a method when executed by the processor, the method comprising;
exploding a recipe for a process to make an end food product, into a set of hierarchical process steps;
obtaining nutrient values for each input material to be used in making the end food product;
obtaining loss profiles for input materials, the nutrient loss profiles including a process loss profile for steps in the process to make the end food product and a storage loss profile for storing intermediate food product resulting during the process; and
performing a hierarchical based nutrient loss calculation using the nutrient values and loss profiles to quantify nutrients remaining in the end food product.

18. The system of example 17 wherein storage losses are calculated on top of process losses, wherein the process loss profile is a percentage of a nutrient value lost during a process step, and wherein a storage loss profile is a percentage of nutrient value lost during storage of a material.

19. The system of example 18 wherein performing a hierarchical nutrient loss calculation comprises building an equation system for each process output, and wherein exploding the recipe results in a graph showing the input and output flows between stages of the recipe.

20. The system of example 19 wherein the equation systems are built into a matrix based on the graph, and wherein the matrix is transformed into reduced row echelon form.

Although a few embodiments have been described in detail above, other modifications are possible. For example, the logic flows depicted in the figures do not require the particular order shown, or sequential order, to achieve desirable results. Other steps may be provided, or steps may be eliminated, from the described flows, and other components may be added to, or removed from, the described systems. Other embodiments may be within the scope of the following claims.

The invention claimed is:

1. A method comprising:
exploding, using a computer system, a recipe for a process to make an end food product, into a set of hierarchical process steps;
obtaining nutrient values for each input material to be used in making the end food product;
obtaining nutrient loss profiles for input materials, the nutrient loss profiles including a process loss profile for steps in the process to make the end food product and a storage loss profile for storing intermediate food product resulting during the process; and
performing, using the computer system, a hierarchical based nutrient loss calculation using the nutrient values and loss profiles to quantify nutrients remaining in the end food product, wherein performing the hierarchical nutrient loss calculation comprises building an equation system for each process output.

2. The method of claim 1 wherein storage losses are calculated on top of process losses.

3. The method of claim 1 wherein the process loss profile is a percentage of a nutrient value lost during a process step to make the end food product.

4. The method of claim 1 wherein a storage loss profile is a percentage of nutrient value lost during storage of a material.

5. The method of claim 1 wherein exploding the recipe results in graph showing input and output flows between stages of the recipe.

6. The method of claim 5 wherein the equation systems are built into a matrix based on the graph.

7. The method of claim 6 wherein the matrix is transformed into reduced row echelon form.

8. The method of claim 1, further comprising:
generating a final calculated nutrient content based on the hierarchical based nutrient loss calculation, wherein the final calculated nutrient content is used to generate a label for the end food product.

9. A non-transitory computer readable storage device having instructions for causing a computer to execute a method, the method comprising:
exploding a recipe for a process to make an end food product, into a set of hierarchical process steps;
obtaining nutrient values for each input material to be used in making the end food product;
obtaining nutrient loss profiles for input materials, the nutrient loss profiles including a process loss profile for steps in the process to make the end food product and a storage loss profile for storing intermediate food product resulting during the process; and
performing a hierarchical based nutrient loss calculation using the nutrient values and loss profiles to quantify nutrients remaining in the end food product, wherein performing the hierarchical nutrient loss calculation comprises building an equation system for each process output.

10. The non-transitory computer readable storage device of claim 9 wherein storage losses are calculated on top of process losses.

11. The non-transitory computer readable storage device of claim 9 wherein the process loss profile is a percentage of a nutrient value lost during a process step to make the end food product.

12. The non-transitory computer readable storage device of claim 9 wherein a storage loss profile is a percentage of nutrient value lost during storage of a material.

13. The non-transitory computer readable storage device of claim 9 wherein exploding the recipe results in a graph showing input and output flow's between stages of the recipe.

14. The non-transitory computer readable storage device of claim 13 wherein the equation systems are built into a matrix based on the graph.

15. The non-transitory computer readable storage device of claim 14 wherein the matrix is transformed into reduced row echelon form.

16. A system comprising:
a processor;
a storage device coupled to the processor, the storage device having a program to perform operations when executed by the processor, the operations comprising;
exploding a recipe for a process to make an end food product, into a set of hierarchical process steps;
obtaining nutrient values for each input material to be used in making the end food product;
obtaining nutrient loss profiles for input materials, the nutrient loss profiles including a process loss profile for steps in the process to make the end food product and a storage loss profile for storing intermediate food product resulting during the process; and
performing a hierarchical based nutrient loss calculation using the nutrient values and loss profiles to quantify nutrients remaining in the end food product, wherein performing the hierarchical nutrient loss calculation comprises building an equation system for each process output.

17. The system of claim 16 wherein storage losses are calculated on top of process losses, wherein the process loss profile is a percentage of a nutrient value lost during a process step to make the end food product, and wherein a storage loss profile is a percentage of nutrient value lost during storage of a material.

18. The system of claim 17 wherein exploding the recipe results in a graph showing input and output flows between stages of the recipe.

19. The system of claim 18 wherein the equation systems are built into a matrix based on the graph.

20. The system of claim 19 wherein the matrix is transformed into reduced row echelon form.

* * * * *